United States Patent [19]

Utermohlen

[11] Patent Number: 5,559,001
[45] Date of Patent: Sep. 24, 1996

[54] MULTI-DOMAIN DNA LIGANDS FOR PROTEIN AND NUCLEIC ACID AFFINITY CHROMATOGRAPHY AND PROCESSING OF SOLID-PHASE DNA

[75] Inventor: Joseph G. Utermohlen, Tucson, Ariz.

[73] Assignee: Arizona Board of Regents for and on behalf of the University of Arizona, Tucson, Ariz.

[21] Appl. No.: 478,049

[22] Filed: Jun. 7, 1995

Related U.S. Application Data

[62] Division of Ser. No. 742,856, Aug. 8, 1991, Pat. No. 5,437,976.

[51] Int. Cl.$^6$ .............................. C12Q 1/68; C12P 19/34; C07H 21/02
[52] U.S. Cl. ..................... 435/6; 435/91.1; 435/91.2; 435/91.4; 536/22.1; 536/24.2
[58] Field of Search .................. 435/6, 91.1, 91.2, 435/91.4

[56] References Cited

U.S. PATENT DOCUMENTS

| | | | |
|---|---|---|---|
| 4,683,202 | 7/1987 | Mullis | 435/91 |
| 4,797,355 | 1/1989 | Stabinsky | 435/6 |
| 5,200,314 | 4/1993 | Urdea | 435/6 |
| 5,437,976 | 8/1995 | Utermohlen | 435/6 |

OTHER PUBLICATIONS

Stamm and Brosius (1991) Sanchored PCR: PCR with cDNA coupled to a solid phase, *Nucleic Acids Research*, 19:1350.
Venetianer and Leder (1974) Enzymatic Synthesis of Solid Phase–Bound DNA Sequences Corresponding to Specific Mammalian Genes, *Proc. Natl. Acad. Sci. USA* 71:3892–3895.
Seed (1982) *Nucleic Acids Research*, 10:1799–1810.
Noyes et al. (1975) Nucleic Acid Hybridization Using DNA Covalently Coupled to Cellulose, *Cell* 5:301–310.
Gilham (1971) Methods in Enzymology 21:191–197.

*Primary Examiner*—W. Gary Jones
*Assistant Examiner*—Amy Atzel
*Attorney, Agent, or Firm*—Oblon, Spivak, McClelland, Maier & Neustadt, P.C.

[57] ABSTRACT

The present invention is directed to a multi-domain oligonucleotide ligand having multiple functions conferred by each of the domains. The ligand is bound to a solid phase matrix for use in both mRNA-affinity chromatography and as a priming matrix for generating matrix-bound cDNA from the mRNA bound to the matrix. The resultant cDNA was tested and found to function as a solid-phase template for PCR. This solid-phase template approach to PCR is demonstrated with oligo-d(T) paper. The functional domains are defined by polynucleotide sequences on the ligand to confer the different functions.

6 Claims, 2 Drawing Sheets

MULTI-DOMAIN DNA LIGANDS FOR PROTEIN AND NUCLEIC ACID AFFINITY CHROMATOGRAPHY AND PROCESSING OF SOLID-PHASE DNA

This is a division, of application Ser. No. 07/742,856 filed on Aug. 8, 1991, now allowed U.S. Pat No. 5,437,976.

BACKGROUND OF THE INVENTION

The present invention relates generally to matrices for conducting messenger RNA (mRNA)-affinity chromatography. More specifically, the present invention relates to a paper matrix which may be used for both mRNA-affinity chromatography and as a priming matrix for generating matrix-bound complementary DNA (cDNA) from the mRNA bound to the matrix.

An organism's traits are encoded in DNA. The information for a specific protein, associated with a particular trait or characteristic, is converted into a second polynucleotide, mRNA, by a process called transcription. This specific bit of information is then translated into the particular protein. Different cells in an organism are specialized to produce only a portion of the proteins encoded in the total DNA complement. Some cells produce as much as 1–2 percent of their total protein as a single species. Generally, mRNA levels reflect this same bias. Hence, if one can start with a population of cells that are preferentially producing the protein of interest and one can produce a double-stranded DNA copy from the mRNA, the gene cloning will have the advantage of starting with a DNA population highly enriched in the desired gene. Moreover, the mRNA that accumulates in the cell and that is subsequently translated into protein is a mature form lacking introns. The double stranded DNA that results also lacks introns and, therefore, contains the amino acid information in an uninterrupted form.

mRNA affinity-chromatography is based on the tendency of complementary, single-stranded nucleic acids to form a double-stranded or duplex structure. Fortunately for the molecular biologist, an enzyme associated with certain animal viruses is capable of using mRNA as a template to generate a complementary piece of DNA. Eukaryotic mRNA typically has a run of adenylic acid residues at its 3' terminus so that a short oligomer of deoxythymidylate can be used as a primer to initiate enzymatic synthesis of cDNA. Because this enzymatic process is based on RNA templates, which is opposite from normal cellular transcription, these enzymes have been named reverse transcriptases. Cloning based on this initial conversion of mRNA to cDNA is termed cDNA cloning. The single-stranded cDNA can be converted into a double stranded DNA using a combination of ribonuclease H and DNA polymerase I. The former degrades the majority of mRNA in the RNA-DNA hybrid leaving short RNA fragments which can act as primers for DNA polymerase I to synthesis of the second DNA strand. This process results in a double-stranded cDNA. The newly-synthesized double-stranded DNA can be cloned into an appropriate plasmid vector for the gene sequence, and introduced and expanded in a typical bacterial host cell.

While there are many cDNA cloning schemes, all start with mRNA enriched for the particular sequence of interest and use enzymatic tools for converting mRNA into double-stranded cDNA. The resulting cDNA clones are typically low yield and must be amplified before identification and verification. The most widely employed method for amplifying cDNA is the polymerase chain reaction (PCR) described in U.S. Pat. Nos. 4,683,202 and 4,683,195, which are hereby incorporated by reference. Amplification of cDNA is accomplished through repeated cycles of DNA synthesis using nucleic acid polymerase enzymes. The steps typically include using Klenow, a large subunit of DNA polymerase I, or any number of heat stable DNA polymerases, i.e., Taq I, in combination with gene specific primers and a DNA template of chromosomal or cDNA origin annealing the primers to the DNA template, in which the enzyme extends the primer sequence by DNA polymerization; and heating the resultant duplexed DNA product to denature and separate the strands, thereby making the strands available for a next cycle of primer annealing and extension. This cycle is repeated continuously until the DNA sequence is present in sufficiently high concentrations to permit identification.

Identification of a cDNA clone typically depends upon hybridization of the clone with labeled oligonucleotides specific for a desired gene or screening of the cells transformed by the hybrids with antibodies specific for the desired protein.

The first step in nucleic acid replication and identification is to sequester mRNA. Gilham first demonstrated the feasibility of isolating polynucleotides by affinity chromatography using oligonucleotide ligands of complementary sequence. A cellulose fiber column matrix was used with a covalently bound homopolymer oligonucleotide ligand. Gilham, P. T., *J. Amer. Chem. Soc.*, 86:4982, 1964; Gilham, P. T., Biochemistry, 7:2809, 1968. In *Methods in Enzymology* 21(P&D): 191–197, 1971 entitled "Resolution of Nucleic Acids," P. T. Gilham published an article entitled "The Covalent Binding of Nucleotides, Polynucleotides, and Nucleic Acids to Cellulose" disclosing the binding of polynucleotides to cellulose through phosphodiester linkages at the 5' or 3' terminals of the polynucleotides. Gilham illustrates the synthesis of thymidine, deoxycytidine and deoxyadenosine polynucleotide celluloses.

Aviv, H. and Leder, P., *Proc. Natl. Acad. Sci. USA*, 69:1408, 1972 used a cellulose fiber column matrix for purifying eukaryotic mRNA using oligo-deoxythymidine (oligo-dT) cellulose. Similar purification schemes have been developed using either an agarose or sepharose dextran polymer matrix with the RNA ligand, polyuridylic acid (poly-U). Conventional mRNA purification methods are performed by column affinity-chromatography using one of these matrices. These conventional methods typically involve forming a duplex between the 3' terminus polyadenylated regions of the mRNA or viral RNA and the oligonucleotide ligand of the oligo-dT or poly-U. High concentrations of monovalent cation drive duplex formation and stability at room temperature. Since the oligonucleotide ligand is bound to an insoluble matrix, the annealed mRNA remains bound to the matrix as long as the column buffer is maintained at a high ionic strength. The mRNA is eluted from the column matrix by denaturing the mRNA-ligand binding duplex by decreasing the ionic strength of the column buffer and raising the column temperature. Thus, mRNA affinity chromatography consists generally of the steps of annealing mRNA to the ligand using high ionic strength buffers, e.g., 0.5M NaCl washing the non-polyadenylated RNA from the column matrix with the same high ionic strength buffer, denaturing the mRNA-ligand binding complex and eluting the mRNA by washing the column matrix with a low ionic strength buffer, e.g., 10 mM Tris/1 mM EDTA (TE buffer).

The use of columns for mRNA affinity chromatography carries with it some important disadvantages. Column chromatography requires specialized equipment, column preparation and mRNA purification is often tedious, time consuming and complex. Packed columns often do not permit large RNA to move freely through the matrix resulting in exclusion and trapping of non-ligand bound RNA within the 25 column matrix. Finally, packed columns often exclude or trap the RNA molecules which hinders the adaptation of this type of chromatography to an automatic format.

Many of these problems have been addressed by attempts to alter the geometry of the packed column by flattening the three dimensional nature of the matrix. The flatter matrix decreases the distance the RNA must diffuse either to interact with the ligand or be freed from the matrix. Wreschner, D. H. and Herzberg, M., *Nucleic Acids Res.*, 12:1349–1359, 1984 disclosed a poly U ligand substituted paper matrix in which the RNA ligand was bound via diazonium linkage with a paper bound arylamine. This poly U paper had a very high affinity for poly A containing nucleic acids. Werner, D., Chemla, Y. and Herzberg, M., *Anal. Biochem.*, 141:329–336, 1984 employed the messenger affinity paper of Wreschner and Herzberg to develop a more simplified process for separating poly-A RNA from total cytoplasmic RNA. Amersham Corporation (Arlington Heights, Ill.) manufactures a paper matrix under the trademark HYBOND-MAP; the only commercially available flat matrix for mRNA affinity chromatography. HYBOND-MAP is a paper matrix composed of a poly-U ligand bound to arylamine substituted cellulose paper. Purifying mRNA using HYBOND-MAP is a simple procedure which does not require specialized equipment. The annealing capacity for mRNA of a 1 $cm^2$ piece of HYBOND-MAP is about 20 µg which is sufficient for most routine analyses. Several samples can be processed simultaneously using separate pieces of poly-U paper. The poly-U ligand used by Wreschner and Herzberg, Werner, Chemla and Herzberg and in the Amersham HYBOND messenger affinity paper is, however, degradable by RNAse or by conditions of high pH, and is, therefore, unsuitable for processes which require alkaline denaturation. The HYBOND messenger RNA affinity paper cannot be easily regenerated for reuse. While the poly-U ligand can be used to prime cDNA synthesis, the utility of the resulting solid phase cDNA is severely limited because of the underlying RNA linkage to the paper matrix. This limitation renders the poly-U papers unsuitable for use as a priming matrix for mRNA-cDNA synthesis for subsequent use as a solid-phase template for PCR and other diagnostic protocols.

Solid-phase cDNA were first made using oligo-d(T) cellulose powder as a primer matrix for hybridizing specifically with mRNA to recover intact mRNA. Venetainer, P. and Leder, P., *Proc. Natl. Acad. Sci. USA*, 71:3892–3895, 1974. These cDNA were used only as specialized affinity-matrix for purifying the corresponding complementary mRNA. Oligo-dT ligand was covalently bound, via phospho-enol binding with the 5' phosphate of the oligomer and the hydroxyl group on cellulose sugar residue, to a loose fiber as a cellulose powder. A slurry of this oligo-dT substituted cellulose powder was packed as a column matrix and used for mRNA affinity chromatography. Substrates and reverse transcriptase enzyme were added to the oligo-dT cellulose and annealed to synthesized solid phase cDNA. This mRNA slurry process for making solid-phase cDNA required relatively large quantities of enzyme and mRNA. The process disclosed by Venetainer and Leder is cumbersome and time-consuming.

It is advantageous, therefore, to provide a solid phase matrix which can be used for both mRNA and viral RNA affinity chromatography and as a priming matrix for cDNA synthesis. The resulting solid phase cDNAs will provide a permanent genetic record of the polyadenylated RNAs in a sample, such as from a eukaryotic organism, blood, tumors, donated organs or any other extractable tissue. Repeated extractions of a sample for nucleic acids will be substantially eliminated because the solid-phase cDNAs can be subjected to several different or repetitive genetic analyses without alteration of the nucleic acid sequence. Rare or scarce nucleic acid information may, in this manner, be preserved and archived for subsequent amplification and study. The solid-phase DNAs may be used as sequence templates for genetic analysis, for disease detection and diagnosis, for gene cloning, or for vaccine development.

SUMMARY OF THE INVENTION

An oligonucleotide ligand is provided which has at least one nucleotide sequence which defines a domain having a first functionality, and at least one nucleotide sequence which defines another domain having a second functionality, distinct from the first functionality. The first functional domain consists of a polynucleotide sequence or sequences which confers a binding function, while the second functional domain consists of a polynucleotide sequence or sequences which confers a reactive domain. The polynucleotide sequence defining the first function domain has a greater binding affinity for a selected solid phase matrix than does the polynucleotide sequence defining the second functional domain.

A solid phase matrix is provided to serve as a binding matrix for mRNA or viral RNA affinity chromatography and as a solid-phase primer for cDNA synthesis. The resultant solid-phase cDNA can be used as a template for the in vitro amplification, detection and diagnosis, gene cloning or genetic analytical processes. For example, an arylamine cellulose paper matrix is diazotized and an oligodeoxythymidine (oligo-d(T))-rich ligand is covalently bound, via diazo linkages, to the paper matrix. The ligand is constructed to have multiple domains, each domain conferring a distinct ligand function. For purposes of illustration, a 25 ligand having two functional domains, i.e., a bifunctional ligand, is discussed. Greater than two functions may be conferred by constructing the ligand with more than two functional domains defined by the nucleotide sequence comprising the functional domain. Thus, in the bifunctional ligand model, the ligand is composed of two distinct domains; a 5' terminal domain and a 3' terminal domain. The 5' terminal domain consists of a 4–12 polyhomonucleotide sequence and the 3' terminal domain consists of about 18–30 polyhomonucleotide sequence, with the 5' terminal domain group having a greater binding affinity for the diazotized paper matrix than the 3' terminal domain group. Specificity for polyadenylated mRNA, which is required in mRNA affinity chromatography, dictates that the 3' terminal domain oligonucleotide consist of deoxythymidylate residues. In this case, the 5' terminal domain will be selected to consist of deoxyguanidylate (d(G)) residues, which have a higher affinity for covalent binding to the diazotized cellulose paper than the oligo-d(T). With 3' oligo-d(T) and 5' oligo-d(G), the guanosine residues bind more efficiently than the thymidylate residues. The oligo-d(G) terminal domain attaches the oligonucleotide ligand to the diazotized paper matrix in an orientation optimal for mRNA affinity chromatography and for priming cDNA synthesis from the 3' polyadenylated terminal domain of the annealed mRNA.

A unique property of the oligo-d(T) paper is that the cDNAs of annealed mRNA may be made using the ligand's oligo-d(T) terminal domain to prime reverse transcriptase-mediated synthesis. These cDNAs are covalently bound to the paper matrix and are useful as gene-sequence templates primers in the polymerase chain reaction, DNA templates for gene cloning, for cloning cDNA libraries, producing expression clones or as hybridization probes.

DETAILED DESCRIPTION OF THE PREFERRED EMBODIMENTS

Figure 1:
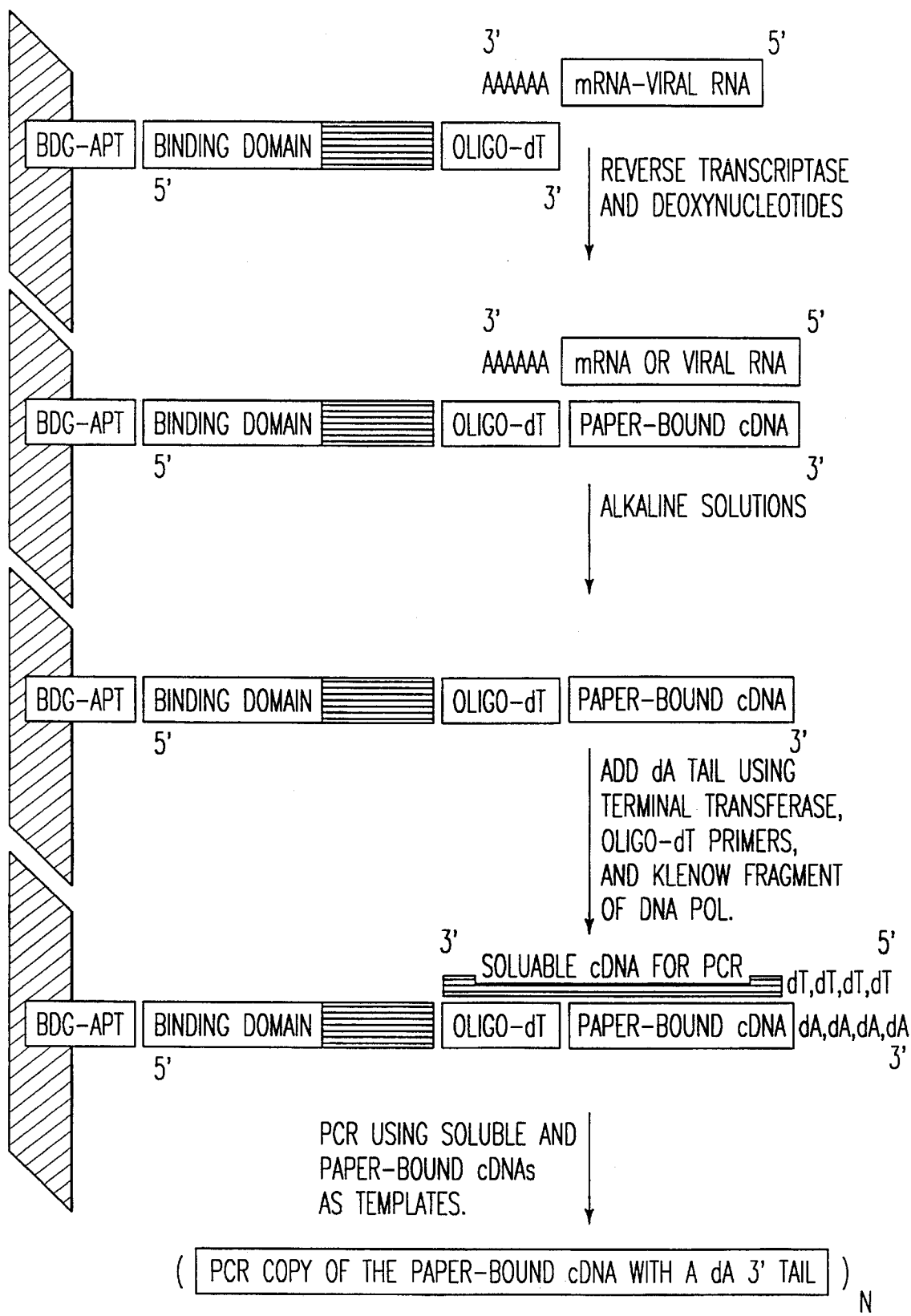
FIG. 1 is a diagrammatic representation of a diagnostic process using the flat solid phase matrix of the invention.

In accordance with a preferred embodiment of the invention there is provided a multi-functional oligonucleotide ligand and a solid phase matrix for use in binding mRNA or viral RNA in RNA affinity chromatography and as a priming matrix for producing cDNAs from the annealed mRNA.

The solid phase binding matrix preferably consists of solid phase arylamines which are capable of forming diazonium bonds with the purine and pyrimidine amines of polynucleotides. Examples of suitable solid phase matrices include i) diazotized arylamine-substitute cellulose papers, such as aminobenzyloxymethyl (ABM) or aminophenylthioether (APT) available under the trademark TRANSABIND from Schleicher & Schuell; ii) ABM or APT prepared in accordance with Seed, *Nucleic Acids Res.*, 10:1799–1810, 1982; iii) diazobenzoylmethyl (DBM) cellulose fibers described by Noyes, B. E. and Stark, G. R., *Cell,* 5:301–310, 1975; iv) bead-type matrixes coated with an arylamine; or v) a matrix in beads, fibers, or woven nylon or other synthetic materials coated with an arylamine. The solid phase matrices provide binding sites for covalently binding polyhomonucleotides. Diazotized cellulose fibers react with the homopolymers poly(U), poly(dT) and poly(G) at neutral pH, but not with poly(A) or poly(C). Noyes, B. E. and Stark, G. R., *Cell,* 5:301–310, 1975.

The oligonucleotide ligand is particularly well suited for use in chromatographic applications and as a solid phase primer for cDNA synthesis to yield solid-phase cDNA. These solid-phase cDNAs can be used as gene specific templates for conducting polymerase chain reactions.

The oligonucleotide ligand is constructed of at least two polynucleotide regions forming functional domains having distinct functionalities. The function of a domain on the ligand is conferred by the polynucleotide sequence of the domain. It is the unique polynucleotide sequence, of the domain, which confers chemical and/or genetic properties unique to the constructed ligand. The ligand may also have multiple separate functional domains, each domain having a functionality conferred by a unique polynucleotide sequence. At least one of the domains is dedicated to binding the ligand to the solid phase matrix, while at least one of the other functional domains is available for reacting with other nucleotides. In this manner, the multi-domain ligand design allows for the creation of new types of chromatographic matrices because the ligand can be covalently bound to the matrix with a specific orientation optimized by the discrete functionalities of the domains on the ligand.

For purposes of example only, a bifunctional ligand was constructed having a 3' terminal domain of deoxythymidylate residues (oligo-d(T)), and a 5' terminal domain of deoxyguanidylate residues (oligo-d(G)). Noyes, B. E. and Stark, G. R., *Cell,* 5:301–310, 1975 teaches that oligo-d(G) has a higher binding affinity for diazotized cellulose fibers than oligo-d(T). The differential binding affinity of the 5' terminal domain oligo-d(G), therefore, provides 5' binding between the oligonucleotide ligand and the diazotized cellulose matrix. The resulting orientation of the 3' oligo-d(T) terminal domain away from the paper surface is optimal for mRNA affinity chromatography and is correct for priming cDNA constructs at the 3' polyadenylated terminal domain of the annealed RNA. Oligo-d(U) may be substituted for the oligo-d(G) while retaining a relative binding affinity differential with the 3' oligo-d(T) terminal domain.

Those skilled in the art will understand that both natural bases and their analogues, such as biotinylated nucleic acids, or arylamine nucleic acids, e.g., arylamineadenosine, N-6-aminohexyldeoxyadenosine, may be used in the construction of the homopolymeric nucleic acids used to form the functional domains of the oligonucleotide ligand. Care must be taken however, to assure that the substitutions be made in positions along the ligand which do not affect the chromatographic properties of the ligand, or the concomitant cDNA constructs from the bound mRNA.

In accordance with a preferred embodiment of the invention, the solid phase matrix is a flat paper-like matrix consisting of a diazotized cellulose paper having a bound oligonucleotide with 5' to 3' directional orientation relative to the binding matrix. It has been found desirable, according to a best mode of the invention, for chromatographic and PCR purposes, that the oligo-d(T) 3' terminal domain consist of about 18–30 oligo-d(T) residues and that the oligo-d(G) 5' terminal domain consist of about 4–12 oligo-d(G) residues.

Other arylamine-substituted matrices may be used. For example, matrices based of plastics, elastomers, cellulose, resins, glucose polymers, polyacrylamides, agarose, rayon, mylon, triacetate, cellulose acetate, or cellulose nitrate may be used.

The foregoing described paper binding matrix is useful for binding with any polyadenylated genomic matter. A nonexhaustive listing of examples of viruses having polyadenylated genomes is set forth in Table 1.

TABLE 1

| Virus Family | Virus or Disease |
| --- | --- |
| coronaviridae | Hepatitis C |
| picornaviridae | foot and mouth disease |
| | hepatitis A |
| | polio |
| | rhinoviruses |
| togaviruses | bovine viral diarrhea |
| | hog cholera |
| | equine encephalitis |
| | rubella virus |
| retroviridae | HIV (Aids) |
| | HTLV |
| | feline leukemia |
| | sarcoma viruses |

A. Chromatographic Properties

By way of example, the affinity of polyadenylated polynucleotides for the paper matrix of the invention was tested using a 390 base polydeoxyadenosine (poly-d(A)). Two types of affinity paper were made by applying an appropriate DNA ligand (5' poly-d(G), 4–12 residues; 3' poly-d(T), 18–30 residues) in 10 µl of 40 mM sodium acetate buffer (pH 4.8) to 0.5 cm² activated APT (diazo form) paper and allowing them to react for 16 hrs at 15° C. The amount of DNA ligand used was varied, 120 picomoles of oligo-d(T)-rich ligand was used to make oligo-d(T) paper and 450 moles of oligonucleotide with the sequence CGTTGAT-AGTTAGACGAACCA, SEQ ID NO: 1 was used to make the control affinity paper. After the binding step, the affinity paper was washed and blocked with a solution of 1M glycine, and 20 mM EDTA (pH 8.9), rinsed in sterile water and stored at −20° C.

The polynucleotide, poly(dA), was labeled with $p^{32}$ (alpha) dATP using terminal deoxytransferase. The specific activity of the labeled poly(dA) was adjusted to approximately 3600 cpm per picomole of poly(dA) by addition of unlabeled poly(dA). The affinity paper was equilibrated with the annealing buffer (0.5 M NaCl mM EDTA, 20 mM Tris, pH 7.5) for 10 min. at room temperature prior to the annealing reaction.

The annealing reaction consisted of applying 150 picomoles of poly(dA) in 10 µl of annealing buffer to 0.5 cm² affinity paper for 5 min at room temperature. The excess solution was removed and saved. The affinity paper was washed for 10 min. in 400 µl of annealing buffer and rinsed in 1 ml of 70% ethanol for 2 min. The annealed poly(dA) was eluted from the affinity paper in 400 µl of 10 mM Tris (pH 7.5) for 30 min at 60° C. Sterile toothpicks were used to transfer the affinity paper between solutions.

The efficiency of the oligo-d(T) paper binding of poly(dA) was determined as a percentage of radioactivity detected in the eluent compared with the total radioactivity applied to the paper during the annealing step. Two different approaches were used to determine the total amount of applied radioactivity. One method was to sum the amount of soluble radioactivity detected in the solutions of each step, a second method was by directly counting the amount of radioactivity in a separate aliquot of poly(dA). The radioactivity recovered at each step was determined by counting five separate, 10 µl aliquots from each fraction. The number of counts-per-minute were multiplied by the dilution factor (40) for direct comparison with the counts-per-minute non-specifically bound to the affinity paper after the elution step and to the toothpicks. Table II below sets forth the averages from tests using three affinity papers with the oligo-d(T) ligand and tests of three affinity papers with the control oligonucleotide ligand.

TABLE II

|  | Oligo-d(T) Paper | Control Paper |
| --- | --- | --- |
| % Radioactivity not bound | 73.4 (6.5)* | 96.1 |
| % Radioactivity eluted | 23.6 (6.2) | 1.2 |
| % Radioactivity on Paper | 2.2 (0.3) | 0.1 |
| % Radioactivity Misc. | 0.7 (0.2) | 2.6 |

From the specific activity of poly(dA), and the determinations of total counts-per-minute used in the annealing step, the foregoing test results indicate that the annealing efficiency of the inventive oligo-d(T) paper is within the range of about 50–70 picomoles of poly(dA) per cm². This range is comparable to that reported for commercially available poly-U messenger RNA affinity papers.

The above-described ligand is bifunctional, i.e., it has a first domain, defined by a polynucleotide sequence, which is dedicated to a matrix binding function, and a second domain, defined by a second polynucleotide sequence, dedicated to a chromatography function. The oligo-d(T) paper is but one example of the multi-domain ligand design concept of the present invention. Ligands designed to have more than two domains may also be made. Such ligands may, for example have guanosine residues throughout the ligand, but separated from the domains needed for matrix binding or chromatography. For these more complex ligands, the binding domain would consist of deoxyuracil residues, with the covalent linkage of the ligand to the arylamine-substituted matrix being based on the reactivity of the cyclic secondary amine of this pyrimidine toward the activated arylamine. The exo-cyclic amines of the guanosine residues, as well as those of cytosine and adenosine, are chemically blocked before binding the ligand to the arylamine matrix. Suitable blocking agents act reversibly only on primary amines and result in derivatizing these bases of the ligands to yield blocked residues such as isobutyrylguanosine or benzoyladenosine. These derivatized bases are then prevented from reacting to the activated arylamine substituted onto the matrix. Thymidine and the deoxyuracil residues are not reactive toward the blocking agent, thus leaving the secondary amines of deoxyuracil to react to the activated arylamine. After these derivatized ligands are bound to the paper, these blocking agents are removed by alkaline-cleavage, leaving these bases in their native form, available for forming duplex with other polynucleotides or intereact with enzymes or other types of proteins.

Thus, in accordance with a preferred embodiment of the invention, there is provided a multi-functional ligand having at least two functional domains, each functional domain having a functionality defined by a polynucleotide sequence in the ligand. The polynucleotide sequences defining the functionalities are selected according to their relative reactivities to the arylamine binding matrix and to other nucleic acids. The inventive ligand is a function-determined construct adapted to optimize ligand function while bound to a solid phase matrix for easy handling and archival storage. The primary-amine-blocking chemistry combined with the multi-domain ligand design facilitates creation of new types of chromatographic matrices because the ligand is covalently bound to the solid phase matrix with a specific pre-determined orientation. With more complex ligand sequences, ligands can be constructed from plasmids or used to isolate DNA binding proteins, e.g., restriction endonucleases.

B. Amplification Properties

The inventive oligonucleotide ligand, bound to the solid phase matrix, may also be used as a solid phase template to amplify a cDNA template using the polymerase chain reaction. Mullis, et al. in U.S. Pat. No. 4,683,195 and 4,683,202 described the original PCR technique which has, to this date, required that the original template be consumed by the reaction. This has made the original amplification template difficult to retrieve or reuse as an original template resource.

Binding the inventive multi-domain ligand to a solid phase matrix preserves the original template and permits the original template to be reused for several different types of analysis, verification of an original analysis, or archival storage of the template for forensic purposes. This ability to preserve and retrieve the original template is believed to be a simple, yet significant, enhancement to the utility of the polymerase chain reaction.

By way of example only, and not to be construed as limiting of the scope of the invention, the bi-functional oligo-d(T) paper, prepared as previously described, was used as an amplification template in the polymerase chain reaction. RNA was extracted from HIV-RF infected cells, and annealed to the oligo-d(T) paper in accordance with the above-described protocol. A cDNA complement of the paper bound RNA was formed by adding reverse transcriptase and deoxynucleotides. Treatment with an alkaline solution removed the template RNA leaving the paper-bound cDNA construct. The polymerase chain reaction using this paper-bound cDNA as template to drive the reaction contained the primers SK38 and SK39 deduced from the gag-pol overlap of HIV I, and using the enzyme Taq I polymerase. This PCR reaction was run for thirty cycles and conducted according to the methodologies of U.S. Pat. Nos. 4,683,202 and 4,683,195, which are hereby incorporated by reference, using the paper-bound cDNA template.

Figure 2:
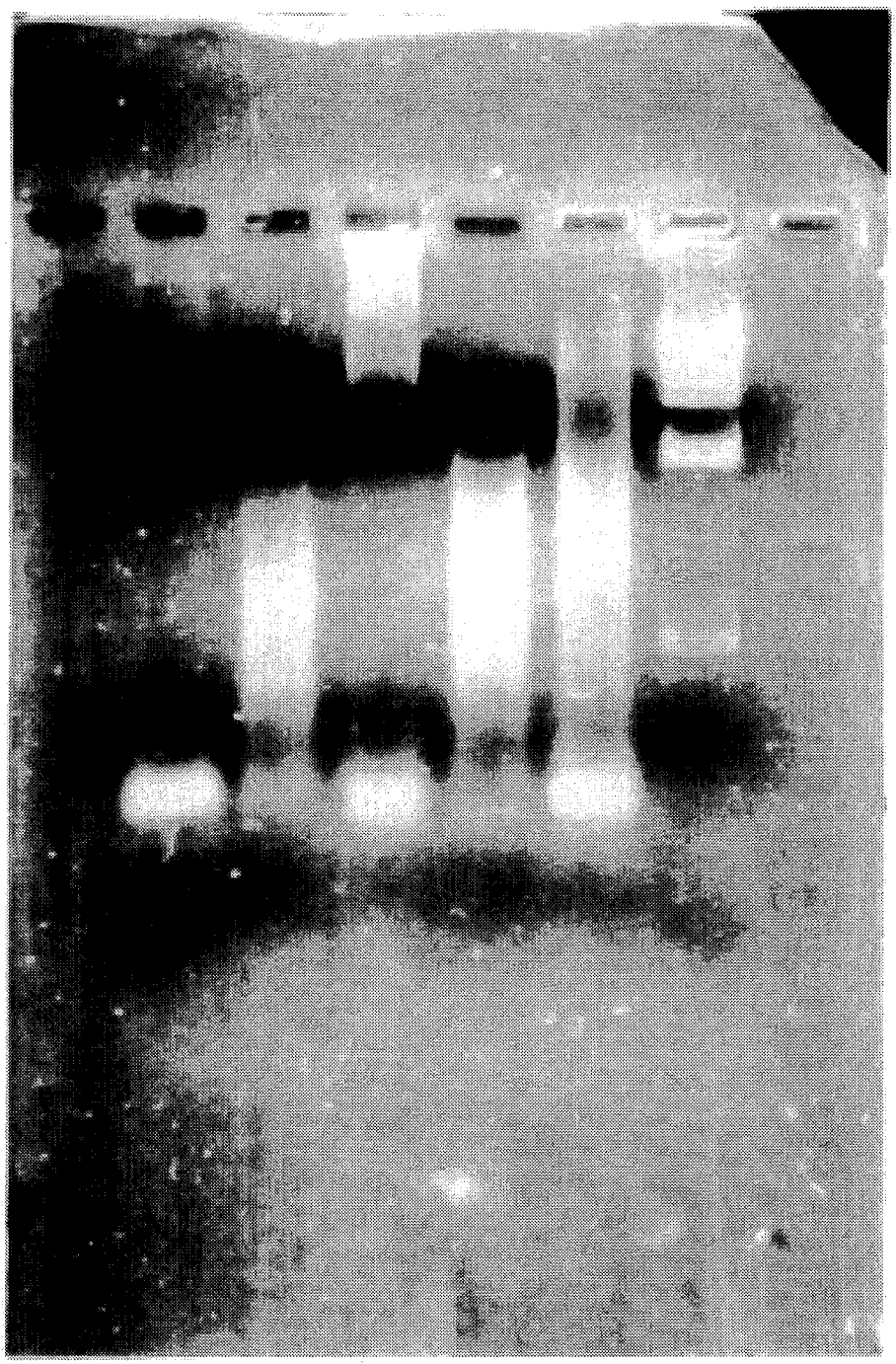
FIG. 2 is an ethidium bromide stain illustrating a thirty-cycle polymerase chain reaction comparing a solid phase cDNA from RNA extracted from HIV-RF infected cells, on oligo-d(T) paper with soluble cDNA.

The results of a test diagnostic PCR reaction are detailed in FIG. 2, which is an ethidium bromide stain showing the sources of the DNA templates for the reaction. Lanes 1 and 5 are 1 ng of plasmid pBKBH10 (HIV-IIIB) run as a standard. Lane 6 is a 123 base pair marker (BRL catalogue #5613, 1989). Lanes 2–4 are cDNA from RNA extracted from HIV-RF-infected cells. The cDNAs in the reactions of Lane 2 are from a poly-A enriched mRNA fraction, and Lane 4 is the total cellular RNA in soluble form. Lane 3 is an equivalent amount of RNA as in Lanes 2 and 4, except that the cDNA is covalently bound to the inventive oligo-d(T) paper. FIG. 2 clearly illustrates the equivalency between a PCR reaction dependent on a cDNA covalently bound to oligo-dT paper (lane 3) and a reaction based on the DNA template generated by conventional cDNA reaction in which the cDNA is in solution (lane 2). The staining pattern indicates that the reaction with the paper-bound cDNA generated less artifact than the reaction with the initial template being soluble cDNA. Both contained the HIV product (199 bp band) though it is easier to resolve from the reaction based on the solid-phase cDNA template. The result seen in Lane 3 is similar to the PCR reaction dependent on a plasmid DNA clone of HIV IIIB. The outermost lanes were not used.

The advantages of the solid phase binding matrix for use in mRNA affinity chromatography and in cDNA construction represents a significant advancement. It has been found that the time needed to conduct a single mRNA affinity chromatography run is substantially reduced and the process simplified. Substitution on the order of $10–9M/cm^2$ and at least 10–20 μg binding of the mRNA to the oligonucleotide ligand has been achieved.

Additional process simplification may be achieved by employing the oligo-d(T) paper of the invention in an automated processing system employing the above-described protocol. Because the oligo-d(T) paper provides a flat solid phase binding matrix, it is well-suited for use in an automated chamber, into which reactants are introduced and withdrawn sequentially to accomplish the steps of mRNA binding, cDNA construction and subsequent amplification under PCR.

The advantage of a matrix-bound template for sequence amplification is that the matrix-bound nucleotide may be archived and be available for multiple analysis or a single sample may be used for a number of different amplification reactions initiated with primers from different gene sequences. Because the template for the amplification reaction is bound to an insoluble matrix, it can be removed from the reaction without altering the template and re-used at a later time.

Thus, in accordance with the preferred embodiments of the invention, there is provided a reusable solid phase matrix for mRNA affinity chromatography and construction of cDNA complements from the paper bound mRNA. The resulting cDNA may then be used as a primer for the polymerase chain reaction, for gene cloning, for detecting pathogens, for diagnosing disease states, for the development of vaccines or for genetic analysis.

The invention has been disclosed and described with reference to its preferred embodiments and the best mode for practicing the invention. The test results are provided as examples of the utility of the invention and are not intended to, nor should be construed to be, limiting of the scope of the invention. Those skilled in the art will understand that the present invention is, of course, in no way restricted to the specific disclosure of the specification, examples and drawings, but also encompasses any modifications within the scope of the appended claims.

What is claimed is:

1. An RNA affinity-chromatography method, comprising the steps of:

(a) providing an arylamine-substituted solid phase binding matrix;

(b) constructing a multi-functional oligonucleotide ligand having a 3' terminal domain comprising polydeoxythymidine and a 5' terminal domain comprising at least one of polydeoxyguanosine, polydeoxyuracil, or poly-N-6-aminohexyldeoxyadenosine;

(c) covalently binding said oligonucleotide ligand to said activated solid phase binding matrix such that said 5' terminal domain is bound to said solid phase binding matrix; and (d) annealing RNA to said multi-functional oligonucleotide ligand bound to said solid phase binding matrix.

2. The method of claim 1, wherein said polydeoxythymidine has from about 18 to about 30 nucleic acid residues and said polydeoxyguanosine, polydeoxyuracil, and poly-N-6-aminohexyldeoxyadenosine each have from about 4 to about 12 nucleic acid residues.

3. The method of claim 1, wherein said arylamine-substituted matrix is selected from the group consisting of arylamine-substituted cellulose, arylamine-substituted plastics, arylamine-substituted elastomers, arylamine-substituted resins, arylamine-substituted glucose polymers, arylamine-substituted polyacrylamides, arylamine-substituted agarose, arylamine-substituted rayon, arylamine-substituted nylon, arylamine-substituted triacetate, arylamine-substituted cellulose acetate, and arylamine-substituted cellulose nitrate.

4. The method of claim 3, wherein said polydeoxythymidine has from about 18 to about 30 nucleic acid residues and said polydeoxyguanosine, polydeoxyuracil, and poly-N-6-aminohexyldeoxyadenosine each have from about 4 to about 12 nucleic acid residues.

5. The method of claim 1, wherein said arylamine-substituted matrix is a cellulose paper selected from the group consisting of aminobenzyloxymethyl-derivatized cellulose paper and aminophenylthioether cellulose paper.

6. The method of claim 5, wherein said polydeoxythymidine has from about 18 to about 30 nucleic acid residues and said polydeoxyguanosine, polydeoxyuracil, and poly-N-6-aminohexyldeoxyadenosine each have from about 4 to about 12 nucleic acid residues.

* * * * *